United States Patent
Shaw

(10) Patent No.: US 9,125,764 B2
(45) Date of Patent: *Sep. 8, 2015

(54) STENT-GRAFT HAVING FACING SIDE BRANCH PORTALS

(71) Applicant: W. L. Gore & Associates, Inc., Newark, DE (US)

(72) Inventor: Edward E. Shaw, Flagstaff, AZ (US)

(73) Assignee: W, L. Gore & Associates, Inc., Newark, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/270,650

(22) Filed: May 6, 2014

(65) Prior Publication Data

US 2014/0243949 A1  Aug. 28, 2014

Related U.S. Application Data

(63) Continuation of application No. 13/287,003, filed on Nov. 1, 2011, now Pat. No. 8,753,386.

(51) Int. Cl.
| | |
|---|---|
| *A61F 2/95* | (2013.01) |
| *A61F 2/954* | (2013.01) |
| *A61F 2/07* | (2013.01) |
| *A61F 2/852* | (2013.01) |
| *A61F 2/856* | (2013.01) |
| *A61F 2/962* | (2013.01) |
| *A61F 2/06* | (2013.01) |
| *A61F 2/89* | (2013.01) |

(52) U.S. Cl.
CPC . *A61F 2/954* (2013.01); *A61F 2/07* (2013.01); *A61F 2/852* (2013.01); *A61F 2/856* (2013.01); *A61F 2/95* (2013.01); *A61F 2/962* (2013.01); *A61F 2/89* (2013.01); *A61F 2002/061* (2013.01); *A61F 2002/067* (2013.01); *A61F 2002/075* (2013.01); *A61F 2002/9522* (2013.01); *A61F 2220/005* (2013.01); *A61F 2220/0033* (2013.01); *A61F 2220/0066* (2013.01); *A61F 2220/0075* (2013.01); *A61F 2250/0007* (2013.01); *A61F 2250/0008* (2013.01); *Y10T 29/49826* (2015.01)

(58) Field of Classification Search
CPC ............. A61F 2/07; A61F 2/856; A61F 2/95; A61F 2/954; A61F 2/962; A61F 2/966
USPC ........................ 623/1.1–1.16, 1.23, 1.27, 1.35
See application file for complete search history.

(56) References Cited

U.S. PATENT DOCUMENTS

| | | |
|---|---|---|
| 5,755,770 A | 5/1998 | Ravenscroft |
| 5,855,598 A | 1/1999 | Pinchuk |
| 5,984,955 A | 11/1999 | Wisselink |
| 6,016,810 A | 1/2000 | Ravenscroft |
| 6,187,033 B1 | 2/2001 | Schmitt et al. |

(Continued)

FOREIGN PATENT DOCUMENTS

WO     2006/034276     3/2006

*Primary Examiner* — Ryan Severson
(74) *Attorney, Agent, or Firm* — Gilbert R. Gabo; David J. Johns

(57) ABSTRACT

In various embodiments, a device for treating disease of a vessel includes a stent graft having an outer surface; and at least two side branch portals each having a proximal end and a distal end. Each distal end is substantially contiguous with the outer surface of the stent graft. In various other embodiments, the distal ends are generally axially further spaced apart than the proximal ends.

23 Claims, 5 Drawing Sheets

(56) References Cited

U.S. PATENT DOCUMENTS

| | | |
|---|---|---|
| 6,210,429 B1 | 4/2001 | Vardi et al. |
| 6,325,826 B1 | 12/2001 | Vardi et al. |
| 6,428,565 B1 | 8/2002 | Wisselink |
| 6,432,131 B1 | 8/2002 | Ravenscroft |
| 6,478,817 B2 | 11/2002 | Schmitt et al. |
| 6,599,316 B2 | 7/2003 | Vardi et al. |
| 6,645,242 B1 | 11/2003 | Quinn |
| 6,723,116 B2 | 4/2004 | Taheri |
| 6,733,522 B2 | 5/2004 | Schmitt et al. |
| 6,770,090 B2 | 8/2004 | Gantt et al. |
| 6,773,453 B2 | 8/2004 | Ravenscroft |
| 6,814,752 B1 | 11/2004 | Chuter |
| 7,144,421 B2 | 12/2006 | Carpenter et al. |
| 7,189,257 B2 | 3/2007 | Schmitt et al. |
| 7,407,509 B2 | 8/2008 | Greenberg et al. |
| 7,413,573 B2 | 8/2008 | Hartley et al. |
| 7,425,219 B2 | 9/2008 | Quadri |
| 7,537,606 B2 | 5/2009 | Hartley et al. |
| 7,645,298 B2 | 1/2010 | Hartley et al. |
| 7,828,837 B2 | 11/2010 | Khoury |
| 7,854,758 B2 | 12/2010 | Taheri |
| 7,976,575 B2 | 7/2011 | Hartley |
| 8,021,419 B2 | 9/2011 | Hartley et al. |
| 8,105,372 B1 | 1/2012 | Chuter |
| 8,128,680 B2 | 3/2012 | Arnault De La Menardiere |
| 8,167,926 B2 | 5/2012 | Hartley et al. |
| 8,257,423 B2 | 9/2012 | Kerr |
| 8,267,988 B2 | 9/2012 | Hamer et al. |
| 8,273,115 B2 | 9/2012 | Hamer et al. |
| 8,287,583 B2 | 10/2012 | LaDuca et al. |
| 8,394,136 B2 | 3/2013 | Hartley et al. |
| 8,474,120 B2 | 7/2013 | Hagaman et al. |
| 8,545,549 B2 | 10/2013 | Hartley et al. |
| 2001/0012962 A1 | 8/2001 | Schmitt et al. |
| 2003/0199967 A1 | 10/2003 | Hartley et al. |
| 2004/0230287 A1 | 11/2004 | Hartley et al. |
| 2005/0131518 A1 | 6/2005 | Hartley et al. |
| 2006/0247760 A1 | 11/2006 | Ganesan et al. |
| 2007/0118208 A1 | 5/2007 | Kerr |
| 2007/0208410 A1 | 9/2007 | Berra et al. |
| 2007/0244547 A1 | 10/2007 | Grennan |
| 2008/0109066 A1 | 5/2008 | Quinn |
| 2008/0269866 A1 | 10/2008 | Hamer et al. |
| 2008/0312732 A1 | 12/2008 | Hartley et al. |
| 2009/0030502 A1 | 1/2009 | Sun et al. |
| 2009/0048663 A1 | 2/2009 | Greenberg |
| 2009/0254172 A1 | 10/2009 | Grewe |
| 2010/0049298 A1 | 2/2010 | Hamer et al. |
| 2010/0292775 A1 | 11/2010 | Kerr |
| 2011/0087318 A1 | 4/2011 | Daugherty et al. |
| 2011/0087319 A1 | 4/2011 | Hagaman et al. |
| 2011/0172762 A1 | 7/2011 | Hartley et al. |
| 2011/0313512 A1 | 12/2011 | Hartley et al. |
| 2012/0046728 A1 | 2/2012 | Huser et al. |
| 2012/0130472 A1 | 5/2012 | Shaw |
| 2013/0211507 A1 | 8/2013 | LaDuca et al. |
| 2013/0218259 A1 | 8/2013 | Quinn |

STENT-GRAFT HAVING FACING SIDE BRANCH PORTALS

BACKGROUND

1. Field

The present disclosure relates to stent grafts for treating disease of the vasculature.

2. Discussion of the Related Art

Disease of the vasculature is increasingly common and, because of the tortuous nature and complexity of the vasculature, is difficult for medical practitioners to treat. By way of example, aortic dissections commonly begin at or near the aortic valve root and continue to the ascending aorta and the aortic arch, and may also affect the upper part of the descending aorta. The three branch vessels off the aortic arch, namely, the brachiocephalic artery and the left common carotid and left subclavian arteries, are anatomically difficult for medical practitioners to access and ultimately treat effectively.

Disease of the vasculature is currently treated surgically (e.g., open repair, endovascular repair, or a hybrid of the two). Surgical approaches to aortic arch repair known in the art include elephant trunk repair and the trifurcated graft technique. However, existing approaches often are highly invasive and/or require specially designed grafts.

There is thus a need in the art for improved, less invasive, and simplified devices, systems and methods for treating disease of the vasculature.

SUMMARY

In various embodiments, devices, systems and methods for treating disease of the vasculature, such as the ascending aorta, aortic arch, and descending aorta, are disclosed. In various embodiments, a stent graft is provided with at least two side branch portals, each having a proximal end and a distal end. The side branch portal's distal end is contiguous with the outer surface of the stent graft. In various embodiments, a side branch portal has an elbow configuration such that its proximal end can be oriented antegrade/retrograde within the stent graft. In yet other various embodiments, a side branch portal has a T-shaped configuration such that its proximal end is split and can be oriented antegrade/retrograde. In various embodiment, one or more side branch portals having a T-shaped configuration are located between outer side branch portals having elbow configurations. In various embodiments, a stent graft comprises side branch portals having elbow configurations with proximal ends facing each other (e.g., antegrade/retrograde). In various embodiments, the distal ends of the side branch portals are generally axially further spaced apart than the proximal ends.

An exemplary system comprises a stent graft having at least two side branch portals as described above, crush loaded, retained by or otherwise housed within a sleeve with a tubular element passing through the side branch portals, so as to preserve a pathway for a branch wire. In an embodiment, the proximal and distal ends of the tubular element extend away from the stent graft through distinct slits in the sleeve. In accordance with an aspect of an embodiment, the distal end of the tubular element is closed.

Another exemplary system comprises a stent graft having at least two side branch portals as described above, together with one or more side branch stent grafts and/or one or more extenders installed at a proximal end of the stent graft.

In accordance with an exemplary method, a stent graft having at least two side branch portals is crush loaded, retained by or otherwise housed within a sleeve and delivered along a guidewire to a treatment location. Once in position, the stent graft may be deployed and side branch stent grafts may be installed at side branch portals.

In exemplary embodiments using a stent graft comprising side branch portals having elbow configurations with proximal ends facing each other, the stent graft may be crush loaded with a tubular element passing through the side branch portals, so as to preserve a pathway for a branch wire. Thereafter, the stent (crush loaded into a sleeve) is delivered along a guidewire to a treatment location, the stent is deployed, and side branch stent grafts can be passed along the branch wire and installed at side branch portals. One or more extenders may be installed at a proximal end of the stent graft as needed.

BRIEF DESCRIPTION OF THE DRAWINGS

The features and advantages of the present disclosure will become more apparent from the detailed description set forth below when taken in conjunction with the drawings.

FIG. 1b illustrates a front view cross section of FIG. 1a.

DETAILED DESCRIPTION OF THE ILLUSTRATED EMBODIMENTS

Figure 1A:
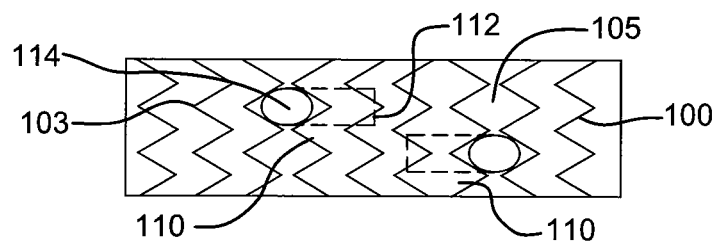
FIG. 1a illustrates a top view of an exemplary stent graft comprising side branch portals having elbow configurations with proximal ends facing each other, aligned on a single or parallel plane.

Persons skilled in the art will readily appreciate that various aspects of the present invention may be realized by any number of methods and apparatuses configured to perform the intended functions. Stated differently, other methods and apparatuses may be incorporated herein to perform the intended functions. It should also be noted that the accompanying drawing figures referred to herein are not all drawn to scale, but may be exaggerated to illustrate various aspects of the present invention, and in that regard, the drawing figures should not be construed as limiting. Finally, although the present invention may be described in connection with various principles and beliefs, the present invention should not be bound by theory.

In accordance with exemplary embodiments, the present invention provides for improved, less invasive, and simplified devices, systems and methods for treating disease of the vasculature. Exemplary embodiments enable branch-to-branch placement of a branch wire, which greatly simplifies placement of side branch stent grafts for installation at side branch portals of a larger stent graft.

The invention will be described primarily with reference to treating disease of the ascending aorta, aortic arch, and descending aorta, however, the invention may be applied to other disease of the vasculature, including, for example, any disease where a larger vessel and one or more branch vessels are to be treated.

Figure 1B:
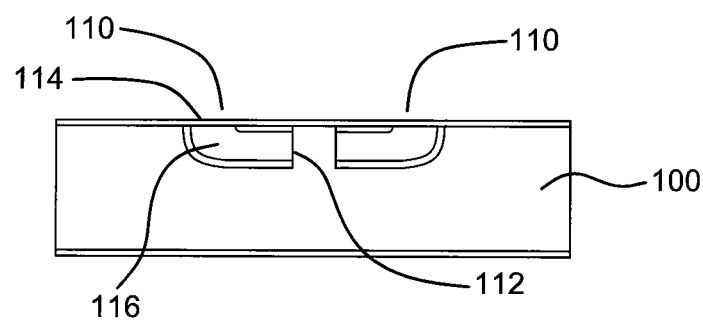

With reference to FIGS. 1a-1b, a stent graft 100, in accordance with various embodiments, has at least two side branch portals 110. In its expanded configuration, an exemplary stent graft diameter may be approximately the same as the vessel to be repaired. In another embodiment, the expanded stent graft diameter may be slightly larger than the vessel to be treated to provide a traction fit within the vessel. Similarly, an exemplary expanded side branch portal diameter may be approximately the same as the vessel to be repaired. Preferably, the cross section is circular, but other cross sections may be suitable including but not limited to profiles that are "D" shaped, oval, triangular, square, polygon shaped or randomly shaped.

The stent graft and side branch portals may comprise materials now known in the art or later discovered, for example, a nitinol helical or ring structure and one or more ePTFE coverings (e.g., one or more coatings on the luminal and/or abluminal surfaces). FIG. 1a, for instance, depicts a stent graft comprising a plurality of zig-zag rings 103 along the length of the stent graft 100, and having ePTFE coverings 105 on the luminal and abluminal surfaces. Other useful materials may comprise nylons, polycarbonates, polyethylenes, polypropylenes, polytetrafluoroethylenes, polyvinyl chlorides, polyurethanes, polysiloxanes, stainless steels, or other biocompatible materials.

The stent graft and side branch portals may be comprised of the same or different materials and may be coupled together as a modular element by now known or as yet unknown methods, for example, by an interference fit, adhesives, sutures, clips or the like. In another embodiment, the stent graft and side branch portals are integrally formed.

In exemplary embodiments, a side branch portal comprises a proximal end 112 and a distal end 114. In exemplary embodiments, a side branch portal's distal end 114 is substantially contiguous with the outer surface of the stent graft 100, while in other embodiment a distal end 114 extends laterally outward from the outer surface of the stent graft 100. Distal ends in exemplary embodiments may be spaced apart, for instance, depending on the spacing between the branch vessels to be treated. A stent graft may comprise two or more side branch portals, and the center points of some or all of their distal ends 114 may be aligned along a single axis that is generally parallel with the longitudinal axis of the stent graft. In other embodiments, with reference to FIG. 1a, a plurality of distal ends 114 of side branch portals 110 are offset, for example, by a distance equal to, or greater than the diameter of the side branch portals themselves at their distal ends (or the largest side branch portal distal end if sized differently).

In exemplary embodiments, and as best seen in FIG. 1b, a side branch portal has an elbow configuration 116 such that its proximal end 112 can be oriented completely or partially antegrade or retrograde within the stent graft 100. Indeed, the inventors have surprisingly found that retrograde perfusion may be at least as effective as antegrade perfusion.

While an "elbow configuration" may correspond to an angle of approximately 90 degrees, larger and smaller angles are also contemplated for use with the present invention. In some embodiments, a side branch portal 110 is not angled; stated differently, the center points of its proximal and distal ends are aligned along a common axis, for example, an axis that is generally perpendicular to the longitudinal axis of the stent graft.

Figure 1C:
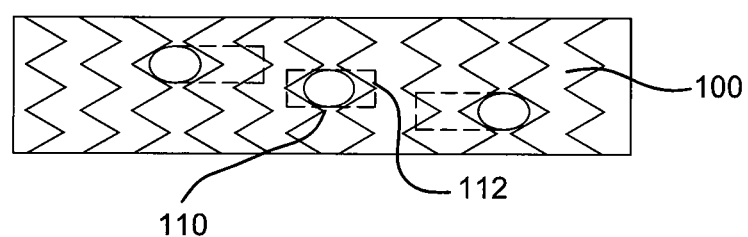
FIG. 1c illustrates a top view of an exemplary stent graft comprising a side branch portal having a T-shaped configuration located between outer side branch portals having elbow configurations.
Figure 1D:
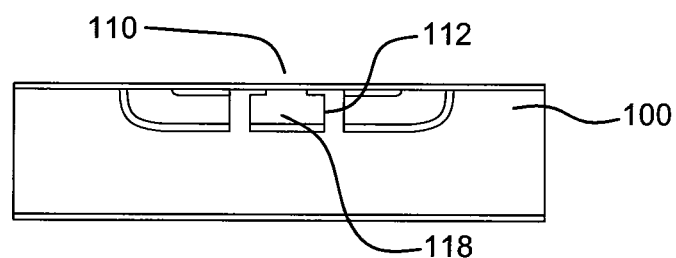
FIG. 1d illustrates a front view cross section FIG. 1c.

Turning to FIGS. 1c-1d, in yet other exemplary embodiments, a side branch portal 110 has a bifurcated configuration (e.g., a T-shaped configuration 118) such that its proximal end 112 is split and can be oriented completely or partially antegrade and retrograde. Stated differently, proximal end 112 may have a plurality of distinct openings, for example, a first opening oriented completely or partially antegrade and a second opening oriented completely or partially antegrade retrograde. Again, angles larger and smaller than approximately 180 degrees are contemplated, but in an exemplary embodiment, the angle between proximal ends is approximately 180 degrees (i.e., the proximal ends face in opposite directions). In one embodiment, one or more unangled side branch portals 110 and/or side branch portals 110 having a T-shaped configuration 118 are located between outer side branch portals 110 having elbow configurations 116.

In a preferred embodiment, a stent graft comprises side branch portals having elbow configurations with proximal ends aligned on a parallel, common or substantially similar plane, facing each other (e.g., one antegrade and the other retrograde, one at an angle relative to antegrade flow and the other at the corresponding angle relative to retrograde flow). Importantly, proximal ends in exemplary embodiments may be spaced apart, for instance, depending on the spacing between the branch vessels to be treated.

Moreover, while the center points of proximal ends may be aligned along a single axis that is generally parallel with the longitudinal axis of the stent graft, proximal ends in exemplary embodiments may be offset, for example, by a distance equal to, or greater than the diameter of the side branch portals themselves at their proximal ends (or the largest side branch portal proximal end if sized differently). By way of illustrations, a side branch portal includes a longitudinal axis extending through the center point of its proximal end. In various embodiments, the longitudinal axes of the side branch portals are not co-axial. In other embodiments, the longitudinal axes of the side branch portals are substantially parallel. In yet other embodiments, the longitudinal axes of the side branch portals are generally parallel with a longitudinal axis of the stent graft. In still other embodiments, the longitudinal axes of the side branch portals are generally aligned along a common plane. In accordance with exemplary embodiments, the distal ends are generally axially further spaced apart than the proximal ends. In yet other embodiments, longitudinal axes of side branch portals are skewed in relation to each other and/or the longitudinal axis of the stent graft.

In various embodiments, the proximal ends may be aligned on a common plane, or on parallel or angled planes, such that a generally clear pathway exists through the portals' proximal ends. It should be understood that the pathway need not be parallel with the longitudinal axis of the stent graft. In an embodiment, one or more side branch portals having a T-shaped configuration are interposed between side branch portals having elbow configurations. In such an embodiment, the pathway through the portals' proximal ends need not be linear.

An exemplary system comprises a stent graft having at least two side branch portals as described above, crush loaded or otherwise collapsed over a tubular element and, retained by or otherwise housed within a sleeve.

The term "tubular element" includes any longitudinally extending structure with or without a through lumen. Thus, tubular elements include but are not limited to tubes with lumens, solid rods, hollow or solid wires (e.g., guidewires), hollow or solid stylets, metal tubes (e.g., hypotubes), polymer tubes, pull cords or tethers, fibers, filaments, electrical conductors, radiopaque elements, radioactive elements and radiographic elements. Tubular elements can be of any material and can have any cross-sectional shape including but not limited to profiles that are circular, oval, triangular, square, polygon shaped or randomly shaped.

The sleeve may be comprised of one or more of nylons, polycarbonates, polyethylenes, polypropylenes, polytetrafluoroethylenes, polyvinyl chlorides, polyurethanes, polysiloxanes, stainless steels, or other biocompatible materials. In yet other embodiments, the sleeve is a tubular element.

Figure 2A:
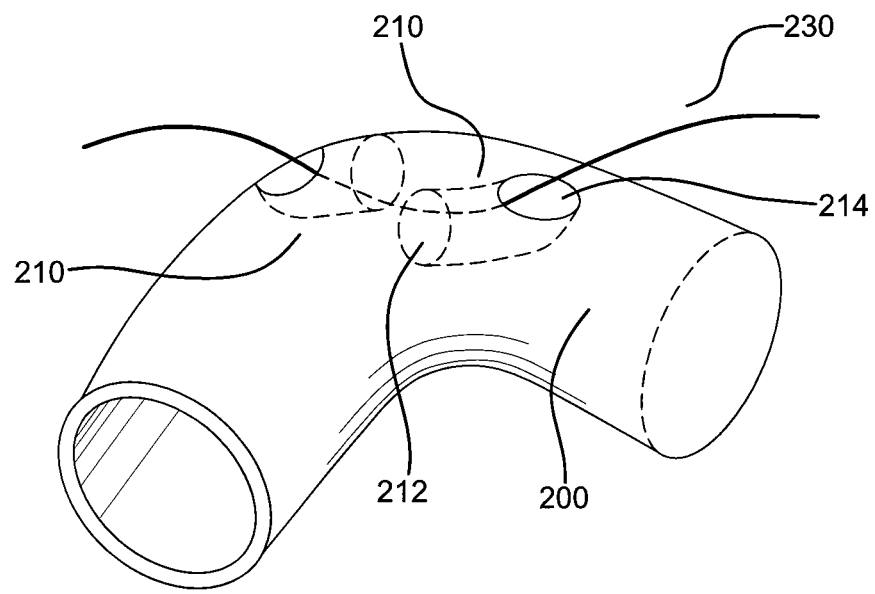
FIG. 2a illustrates a branch wire threaded through exemplary side branch portals having elbow configurations with proximal ends facing each other.
Figure 2B:
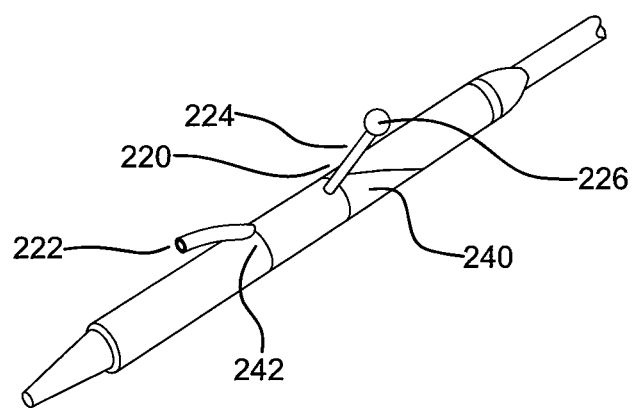
FIG. 2b illustrates an exemplary delivery configuration wherein the stent graft is crush loaded with a tubular element passing through the side branch portals.

Making reference to FIGS. 2a-2b, in exemplary embodiments, a stent graft 200 is crush loaded and constrained by a constraining sleeve 240 with one or more tubular elements 220 passing through some or all of the side branch portals 210, so as to preserve a conduit there through (e.g., a pathway for a branch wire 230). Stated differently, a lumen through some or all of the side branch portals 210 may be preserved which guides a guidewire while the stent graft 200 remains constrained by the constraining sleeve 240. In this embodiment, the tubular element 220 may be threaded (passed through) in the distal end 214 and out the proximal end 212 of one side branch portal 210 and in the proximal end 212 and out the distal end 214 of another side branch portal 210. In some embodiments, the tubular element is additionally threaded through proximal ends of one or more side branch portals having a T-shaped configuration.

In an embodiment, the proximal end 222 and distal ends 224 of a tubular element 220 extend out opposite distal ends of the side branch portals and away from the stent graft through the sleeve 240. Passage through the sleeve may be accomplished by various configurations including but not limited to one or more slits 242, holes, windows, voids, etc. in the sleeve suitable for passage of the tubular element. In an embodiment, the alignment of the slit 242 is selected to prevent tearing of the sleeve 240. Passage may also be accomplished through a plurality of sleeves, for example, a central sleeve and two lateral sleeves. Here, the proximal end 222 and distal ends 224 of a tubular element 220 extend out opposite distal ends of the side branch portals generally at the junctions between the central sleeve and two lateral sleeves.

In accordance with an aspect of an embodiment, the distal end 224 of the tubular element 220 is closed to block passage of an inner tubular element (e.g., a guidewire). Limiting advancement of the inner tubular element through the side branch portals in this manner may facilitate removal of the tubular element 220 from the constrained stent graft. The distal end may be closed in various embodiments by heat sealing, or by using an end cap, plug or the like, shown for illustration purposes as reference numeral 226.

Other exemplary systems comprise a stent graft having at least two side branch portals as described above, together with one or more side branch stent grafts and/or one or more extenders installed at a proximal end of the stent graft. Exemplary side branch stent grafts may be independent or connected to each other, as will be discussed below. Exemplary extenders include aneurysmal and coronary extenders, as will also be discussed below.

Exemplary methods for use in connection with the devices and systems will now be described, however, they should not be construed as limiting the scope of the present invention, but rather as illustrative.

In accordance with one exemplary method, a guidewire is tracked from an anatomical access (e.g., a fenestration or opening in an artery or vein) through the vasculature to an anchoring location, located distal to a treatment location, using now known or as yet unknown techniques. The distal end of the guidewire is then anchored at the anchoring location, again, using now known or as yet unknown methods, such as a balloon catheter.

Next, a stent graft having at least two side branch portals, as described herein, is crush loaded or otherwise collapsed over a tubular element and, retained by or otherwise housed within a sleeve, and delivered along the guidewire to the treatment location.

Optimal positioning of the stent graft may be determined by various now known or as yet unknown techniques. By way of example, radiopaque markers or indicators can be incorporated into the stent graft, side branch portals or the tubular element(s) to facilitate placement and visualization within the vasculature. Fluoroscopic visualization, contrast injection and/or other technologies known in the art may also be used to assist in positioning of the stent graft.

Once in position, the stent graft is deployed by removing the sleeve, after which one or more side branch stent grafts may be installed at side branch portals, typically through the side branch(es) to be treated.

Figure 3:
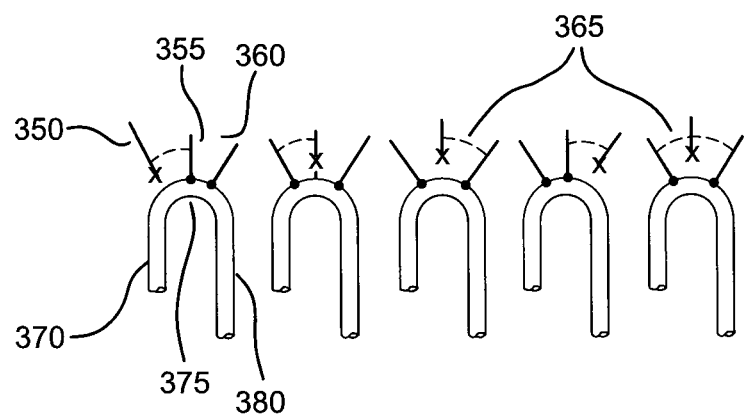
FIG. 3 illustrates exemplary aortic arch bypass configurations.

Exemplary methods for treating disease of the ascending aorta, aortic arch, and descending aorta will now be described. With reference to FIG. 3, an ascending aorta 370, aortic arch 375, and descending aorta 380 are shown. With continued reference to FIG. 3, a medical practitioner may diagnose disease of the brachiocephalic artery 350 or the left common carotid artery 355 or left subclavian artery 360. The practitioner may perform a single bypass 365 or double bypass 365 and may desire to deploy a stent graft in the aortic arch 375 and treat each of the disease free branch vessels off the aortic arch with a side branch portal.

Figure 4:
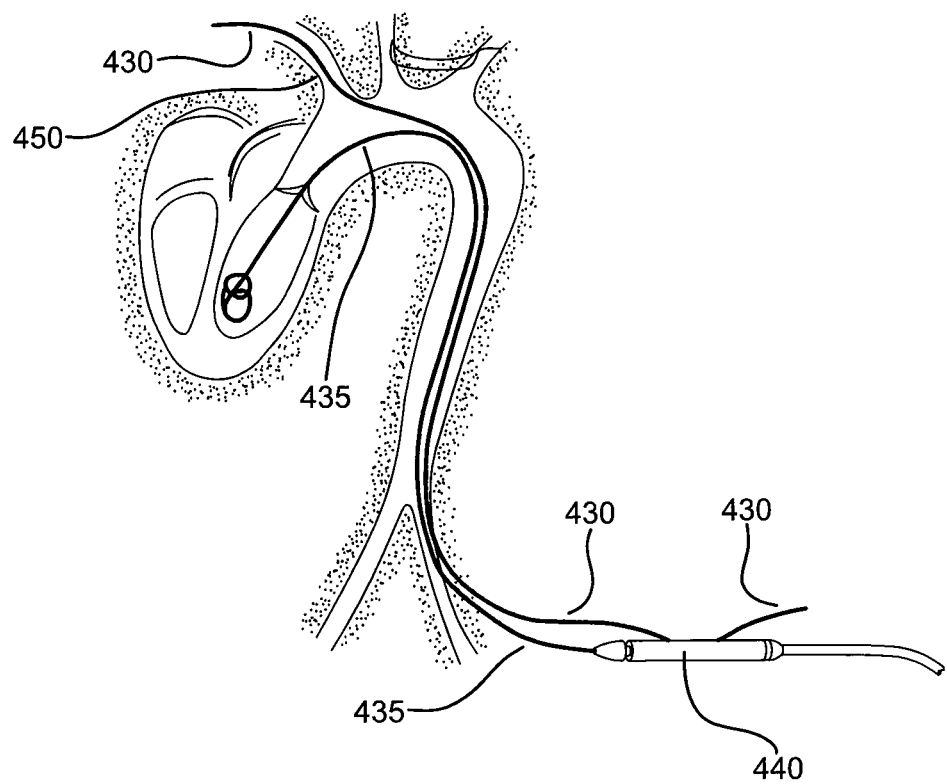
FIG. 4 illustrates a method comprising a guidewire and a branch wire in accordance with an exemplary embodiment.

Turning to FIG. 4, in accordance with one exemplary method, a guidewire 435 is tracked from an incision in the femoral artery through the aorta to the left ventrical using now known or as yet unknown techniques. The distal end of the guidewire 435 is then anchored within the left ventrical, again, using now known or as yet unknown methods, such as a balloon catheter.

A branch wire 430 is then tracked from an incision in a branch vessel to be treated (the brachiocephalic artery 450 in FIG. 4) through the aorta to the incision in the femoral artery using now known or as yet unknown techniques. More than one branch wire 430 may be used, for example, in connection with a stent graft comprising one or more side branch portals having a T-shaped configuration located between outer side branch portals having elbow configurations. In this manner, more than two branch vessels may be treated.

Next, a stent graft having at least two side branch portals (corresponding to the two disease free branch vessels off the aortic arch), as described herein, is crush loaded or otherwise collapsed over a tubular element and, retained by or otherwise housed within a sleeve 440. In various embodiments and as described above, the side branch portals have proximal ends aligned on a parallel, common or substantially similar plane, facing each other. The proximal and/or distal ends of the side branch portals may or may not be offset, as discussed above.

The stent graft is crush loaded with a tubular element passing through the side branch portals, so as to preserve a pathway for the branch wire through the side branch portals. In embodiments comprising one or more side branch portals having a T-shaped configuration located between outer side branch portals having elbow configurations, more than one tubular element may passing through the stent graft and side branch portals, so as to preserve multiple pathways for multiple branch wires through the side branch portals. The proximal and distal ends of the tubular element(s) extend out distal ends of the side branch portals and away from the stent graft through a slit in the sleeve.

As the crush loaded stent graft is delivered along the guidewire to the aortic arch, the branch wire 430 is threaded through the side branch portals via the tubular element. In some embodiments, the distal end of the tubular element may be capped such that the tubular element is pushed completely out of the side branch portals and stent graft upon threading of the branch wire.

Figure 5A:
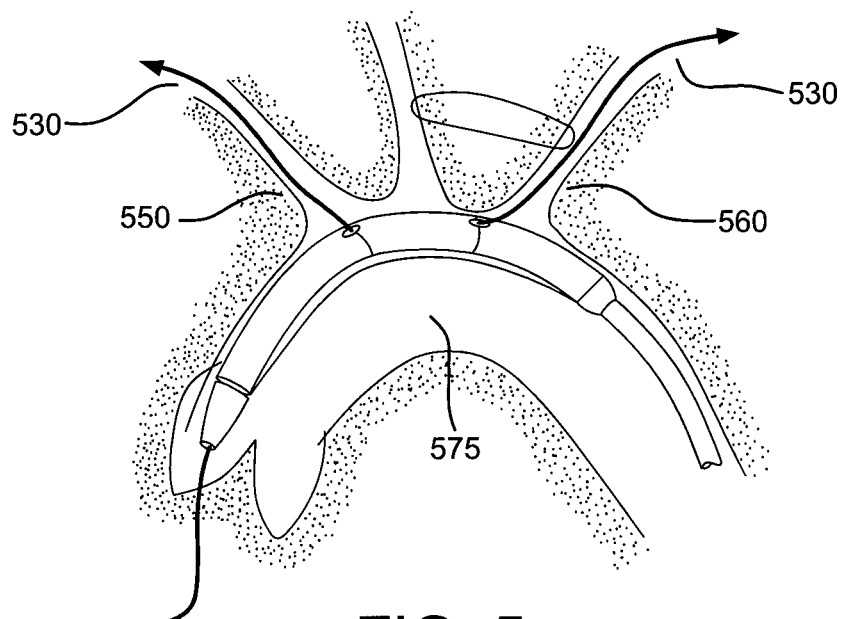
FIG. 5a illustrates a crush loaded stent graft at a treatment location in accordance with an exemplary embodiment.
Figure 5B:
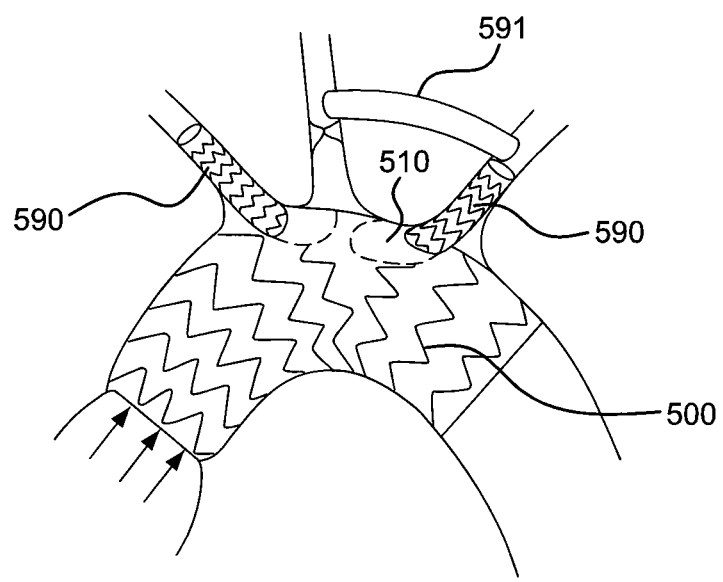
FIG. 5b illustrates a deployed stent graft with side branch stent grafts at a treatment location in accordance with an exemplary embodiment.

With reference to FIGS. 5a-5b, the stent graft 500 is thus delivered to the aortic arch 575 in its compressed configuration. As described above, optimal positioning of the stent graft may be determined by various now known or as yet unknown techniques.

Once optimally positioned, the end of the branch wire 530 extending into the femoral artery can be snared out another branch vessel to be treated (the left subclavian artery 560 in FIG. 5a). A loop snare may be used for this purpose, or any other snare method now known in the art or later discovered. In embodiments having more than one tubular element and more than one branch wire for the treatment of more than two branch vessels, similar snaring techniques may be used to snare the end of each branch wire 530 extending into the femoral artery out the particular branch vessel to be treated.

Traction is optionally applied to the ends of the branch wire(s) to position the stent graft so it is "snug" along the outer curvature of the aortic arch 575.

Turning to FIG. 5b, in exemplary embodiment, the stent graft is then deployed by removing the sleeve. Sleeve removal may be accomplished by various now known or as yet unknown methods, such as a pull cord extending through the femoral access. In an embodiment, the stent graft may be deployed by simply unstitching the sleeve. Stated differently, it may not be necessary to remove the sleeve in an embodiment.

Figure 6A:
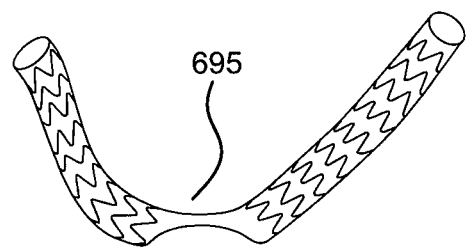
FIG. 6a illustrates an exemplary mono-branch.

Finally, one or more side branch stent grafts 590 may be installed at side branch portals 510 of stent graft 500. With momentary reference to FIG. 6a, in one embodiment, a plurality of side branch stent grafts 590 are interconnected to each other, for example, by a bridge 695.

Turning back to FIG. 5a-5b in exemplary embodiments, side branch stent grafts 590 are passed along the branch wire 530 through the side branch vessels 550 and 560 to be treated. With reference to FIG. 5b, care may be taken so that a side branch stent graft 590 does not extend beyond a bypass graft 591. A side branch stent graft 590 may be crush loaded or otherwise collapsed over a tubular element and, retained by or otherwise housed within a sleeve. Side branch stent grafts 590 may be coupled at side branch portals by now known or as yet unknown methods, for example, by an interference fit, adhesives, sutures, clips or the like.

One or more extenders may be installed at a proximal and/or distal end of the stent graft as needed. In general, an extender may extend the stent graft closer to the aortic valve root and beyond, for example, to the coronary arteries. Similar to a stent graft within the spirit and scope of the invention, an extender may be comprised of materials now known in the art or later discovered, for example, a nitinol helical or ring structure and one or more ePTFE coverings. Other useful materials may comprise nylons, polycarbonates, polyethylenes, polypropylenes, polytetrafluoroethylenes, polyvinyl chlorides, polyurethanes, polysiloxanes, stainless steels, or other biocompatible materials.

Figure 6B:
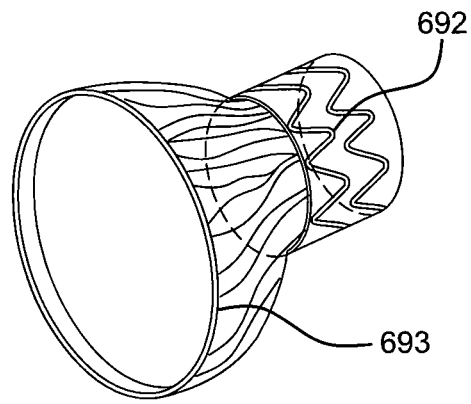
FIG. 6b illustrates an exemplary aneurysmal extender.
Figure 6C:
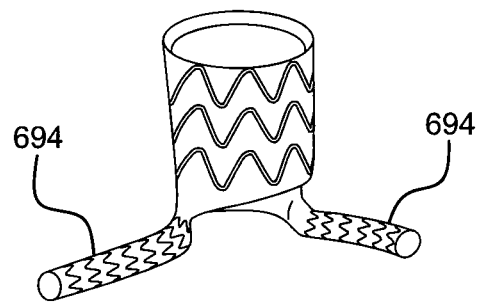
FIG. 6c illustrates an exemplary coronary extender.

Extenders may be coupled to the stent graft prior to insertion or advanced along the guidewire through the lumen of the stent graft subsequent to its radial deployment. Exemplary extenders include aneurysmal and coronary extenders, as shown in FIGS. 6b and 6c, respectively.

An exemplary aneurysmal extender may comprise a radial stiff portion 692 and a radial compliant portion 693 having an increasing, frustoconical style diameter, and being configured to seal with minimum force.

An exemplary coronary extender may comprise one inside the other. An exemplary coronary extender may comprise one or more side branch stent grafts 694 to be installed in one or more coronary arteries. In embodiments comprising a coronary extender, a guidewire may be inserted into the coronary arteries to guide placement of the extender.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A system for treating vascular disease, said system comprising:
   a catheter;
   a stent graft having at least a pair of side branch portals, each of the pair of side branch portals having two ends, with one end being substantially contiguous with the outer surface of the stent graft;
   the stent graft constrained onto a catheter for endoluminal delivery of the stent graft; and
   a guidewire tube that extends through each pair of side branch portals and preserves a lumen which guides a guidewire through each pair of side branch portals while the stent graft remains constrained by the constraining sleeve, wherein an end of the guidewire tube is closed to limit advancement of the guidewire therethrough while the guidewire tube extends through each pair of side branch portals of the constrained stent graft.

2. The system as set forth in claim 1, wherein the guidewire tube is removable after the guidewire is received therethrough.

3. The system as set forth in claim 1, wherein opposite ends of the guidewire tube extend away from the stent graft through distinct slits in the constraining sleeve.

4. The system as set forth in claim 1, further comprising one or more side branch stent grafts installed at each pair of side branch portals.

5. The system as set forth in claim 1 further comprising at least one side branch stent graft extending through at least one of the side branch portals for treating a branch vessel.

6. The system as set forth in claim 1 further comprising at least two side branch stent grafts extending respectively through each pair of side branch portals.

7. The system as set forth in claim 6, wherein two of the at least two side branch stent grafts are interconnected.

8. The system as set forth in claim 1, further comprising an extender installed at a proximal end of the stent graft.

9. The device as set forth in claim 1, wherein each side branch portal includes a longitudinal axis extending through the center point of its respective proximal end.

10. The device as set forth in claim 9, wherein the longitudinal axes of each of the pair of side branch portals are generally aligned along a common plane.

11. The device as set forth in claim 9, wherein the longitudinal axes of each of the pair of side branch portals are not co-axial.

12. The device as set forth in claim 11, wherein the longitudinal axes of the side branch portals are substantially parallel.

13. The device as set forth in claim 11, wherein the longitudinal axes of the side branch portals are generally parallel with a longitudinal axis of the stent graft.

14. The device as set forth in claim 1, wherein each side branch portal pair includes a first end that is substantially contiguous with the outer surface of the stent graft and an opposite second end, the second end of one of the pair of side branch portals faces antegrade.

15. The device as set forth in claim 1, wherein each side branch portal pair includes a first end that is substantially contiguous with the outer surface of the stent graft and an opposite second end, the second end of one of the pair of side branch portals faces retrograde.

16. The device as set forth in claim 1, wherein each side branch portal pair includes a first end that is substantially contiguous with the outer surface of the stent graft and an opposite second end, the second end of one of the pair of side branch portals faces antegrade and the second end of the other of the pair of side branch portals faces retrograde.

17. The device as set forth in claim 1, wherein at least one of the pair of side branch portals comprises a bifurcated configuration.

18. The device as set forth in claim 17, wherein the side branch portal having the bifurcated configuration is generally T-shaped.

19. The device as set forth in claim 1 including a third side branch portal having a T-shaped configuration and being disposed between the pair of side branch portals.

20. The device as set forth in claim 19, wherein each pair of side branch portals are generally elbow-shaped.

21. The device as set forth in claim 1, wherein at least one side branch portal is generally elbow-shaped.

22. The device as set forth in claim 1 including a constraining sleeve for constraining the stent graft onto the catheter for endoluminal delivery of the stent graft, wherein opposite ends of the guidewire tube extend outside of the constraining sleeve.

23. A method of assembling a system for treating vascular disease, said method comprising:
    providing a catheter;
    providing a stent graft having at least a pair of side branch portals, each of the pair of side branch portals having two ends, with one end being substantially contiguous with the outer surface of the stent graft;
    constraining the stent graft with a constraining sleeve on an end of the catheter for endoluminal delivery of the stent graft;
    providing a guidewire tube, wherein an end of the guidewire tube is closed to limit advancement of the guidewire therethrough while the guidewire tube extends through each pair of side branch portals of the constrained stent graft; and
    extending the guidewire tube through each pair of side branch portals and thereby preserving a lumen for guiding a guidewire through each pair of side branch portals while the stent graft remains constrained by the constraining sleeve.

* * * * *